United States Patent [19]

Villamarin

[11] Patent Number: 5,585,094
[45] Date of Patent: Dec. 17, 1996

[54] COMPOSITIONS AND METHODS FOR TREATING HAIR USING A MIXTURE OF POLYSILOXANES

[75] Inventor: Arturo A. Villamarin, Grand Rapids, Mich.

[73] Assignee: The Dial Corp, Phoenix, Ariz.

[21] Appl. No.: 511,284

[22] Filed: Aug. 4, 1995

Related U.S. Application Data

[62] Division of Ser. No. 22,828, Feb. 24, 1993, Pat. No. 5,439,677, which is a continuation of Ser. No. 633,498, Dec. 26, 1990, abandoned, which is a continuation-in-part of Ser. No. 383,499, Jul. 24, 1989, abandoned, Ser. No. 383,500, Jul. 24, 1989, abandoned, Ser. No. 593,580, Oct. 9, 1990, abandoned, and Ser. No. 600,153, Oct. 19, 1990, abandoned, which is a continuation of Ser. No. 383,501, said Ser. No. 593,580, is a continuation of Ser. No. 383,509, Jul. 24, 1989, abandoned.

[51] Int. Cl.$^6$ .............................. A61K 7/035; A61K 7/11
[52] U.S. Cl. .................. 424/70.12; 424/70.122; 424/DIG. 2; 525/474
[58] Field of Search ............................ 424/78.08, 70.12, 424/70.122, 78.19, DIG. 2; 525/474; 514/772; 528/31–34

[56] References Cited

U.S. PATENT DOCUMENTS

| | | | |
|---|---|---|---|
| 2,807,601 | 9/1957 | Dennett | 428/266 X |
| 3,127,363 | 3/1964 | Nitsche et al. | 525/477 X |
| 4,902,499 | 2/1990 | Bolish, Jr. et al. | 424/70 |

OTHER PUBLICATIONS

'Dow Corning Silicone Products' 7 pp ©1987 Dow Corning Corporation.

*Primary Examiner*—Edward J. Webman
*Attorney, Agent, or Firm*—Bernard L. Howard

[57] ABSTRACT

Methods and compositions for semi-permanently conditioning hair by treating the hair, preferably following shampooing, with a composition including a low viscosity oil-in-water emulsion of a mixture of two polysiloxane polymers, that is, a hydroxy terminated dimethyl polysiloxane and a methyl hydrogen polysiloxane, the composition being at an acid pH. It is a feature of this invention that the polysiloxane polymers in the hair-treating composition are in an unreacted or non-crosslinked state. After the composition is applied to the hair, the crosslinking of the two polysiloxane polymers takes place on the hair resulting in a semi-permanent conditioning effect. Although some crosslinking of the polymers will occur while drying the treated hair at room temperatures, increased crosslinking occurs when the hair is blow dried using heated air.

6 Claims, 2 Drawing Sheets

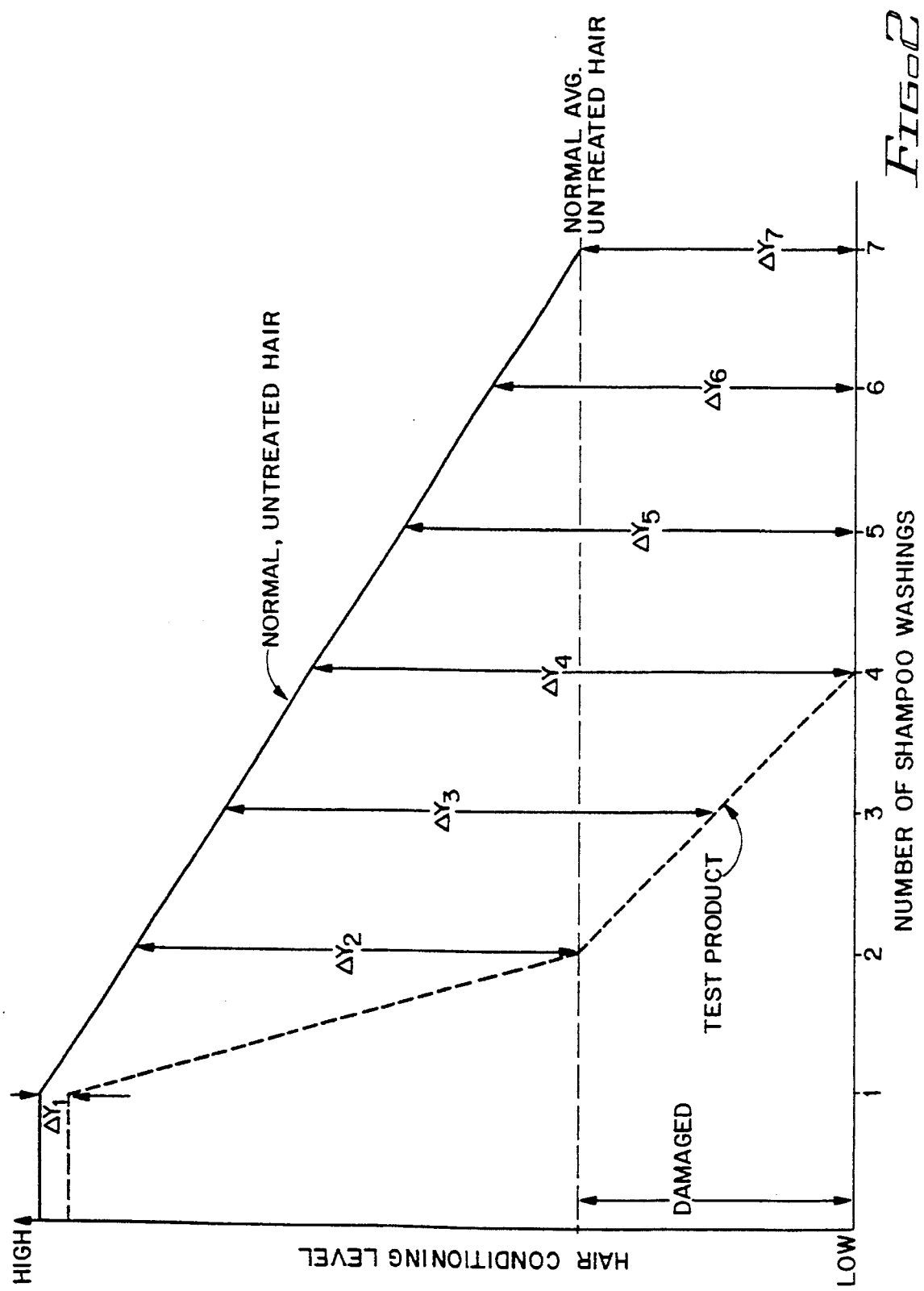

COMPOSITIONS AND METHODS FOR TREATING HAIR USING A MIXTURE OF POLYSILOXANES

RELATED APPLICATIONS

This application is a division of application Ser. No. 08/022,828, filed on Feb. 24, 1993, now U.S. Pat. No. 5,439,677, which in turn is a continuation of application Ser. No. 07/633,498 filed Dec. 26, 1990 abandoned which in turn is a continuation-in-part of the following applications: Ser. No. 07,383,499 filed Jul. 24, 1989 abandoned; Ser. No. 07/383,500 filed Jul. 24, 1989 abandoned; Ser. No. 07/593,580 filed Oct. 9, 1990 abandoned which in turn is a continuation of application Ser. No. 07/383,509, filed Jul. 24, 1989, now abandoned; Ser. No. 07/600,153 filed Oct. 19, 1990 which in turn is a continuation of application Ser. No. 07/383,501, now abandoned.

FIELD OF THE INVENTION

The present invention relates to compositions and methods for treating hair and more particularly to compositions containing a blend of a hydroxy-terminated polysiloxane polymer and a reactive methyl hydrogen polysiloxane and methods for treating hair with said compositions whereby crosslinking of said polymers takes place on the hair resulting in long lasting hair conditioning.

BACKGROUND OF THE INVENTION

Hair in its natural state is rather impervious to damage. However, due to environmental conditions as well as the abuse to which it is usually subjected, hair can wear out at abnormal rates, causing its natural shield —the cuticle— to fall out and the cortex to shatter ending in breakage. Hair treating compositions and conditioners in particular, are designed to attempt to prevent or restore this damage. State-of-the-art products achieve these goals with various degrees of success, but all fail at providing the benefit for prolonged periods of time, particularly, after shampooing previously treated hair.

A typical high quality hair conditioner is expected to provide benefits to the hair such as detangling and low comb drag, among others, without imparting an unnatural or greasy feel to the hair. The conditioning effect also should not interfere with setting of the hair, i.e., it should not diminish the hair's ability to retain curl or hair style. Further, a conditioner should not make the hair stringy or dull a few hours after application. The dulling effect of some conditioners can occur by wicking the natural oils from the scalp up the hair shaft or by attracting dirt.

Hair conditioners formulated with ingredients containing functional groups substantive to the hair such as quaternized proteins, quaternized amines, amine oxides or silicone polymers with amino functional groups tend to be substantive to the hair to varying degrees. Substantivity is the capacity of a substance to absorb/adsorb to a surface. In general, hair substantivity for conditioning ingredients increases with more hydrophobic character, higher molecular weight, and higher charge densities (with positively charged molecules).

Most of these ingredients provide acceptable conditioning benefits to varying degrees, but fail to provide a longer-lasting clean feeling while providing long lasting conditioning benefits. As a rule of thumb, it can be stated that the greater the substantivity of the conditioning ingredient, the greater the likelihood it will impart a greasy coated feel to the hair or more generally, an unnatural feel and appearance. With some ingredients, over-conditioning and build-up is the result. The build-up effect is manifested as the inability of the hair to hold a set and/or by having a matted stringy look. Heretofore the difficulty in developing products with residual action and good performance without debilitating negative effects, as described, has limited the ability of hair product formulators and marketers to provide a product the consumer does not have to use every time he or she uses shampoo.

It is therefore an object of this invention to provide methods for treating hair employing a composition containing a blend of two polysiloxane polymers whereby crosslinking of the polymers takes place on the hair.

It is a further object of this invention to provide hair-treating compositions which contain a low viscosity emulsion of a reactive hydroxy terminated dimethyl polysiloxane and a reactive methyl hydrogen polysiloxane, said polysiloxanes being unreacted in the composition.

It is a still further object of this invention to provide hair treating compositions and methods which provide good conditioning benefits for prolonged periods of time, particularly after repeated shampooing.

It is another object of this invention to provide a hair treating composition which is highly substantive to hair, and provides long lasting hair conditioning properties without build-up or over conditioning.

SUMMARY OF THE INVENTION

The foregoing objectives and others are accomplished by treating the hair, preferably following shampooing, with a composition including a low viscosity oil-in-water emulsion of a mixture of two polysiloxane polymers, that is, a hydroxy terminated dimethyl polysiloxane and a methyl hydrogen polysiloxane, the composition being at an acid pH. It is a feature of this invention that the polysiloxane polymers in the hair-treating composition are in an unreacted or non-crosslinked state. However, after the composition is applied to the hair, the crosslinking of the two polysiloxane polymers takes place on the hair resulting in a semi-permanent conditioning effect. Although some crosslinking of the polymers will occur while drying the treated hair at room temperatures, increased crosslinking occurs when the hair is blow dried using heated air.

BRIEF DESCRIPTION OF THE DRAWINGS

FIG. 2 demonstrates the effect of hair conditioning compositions on damage to hair by repeated washings.

DETAILED DESCRIPTION OF THE INVENTION

Figure 1:
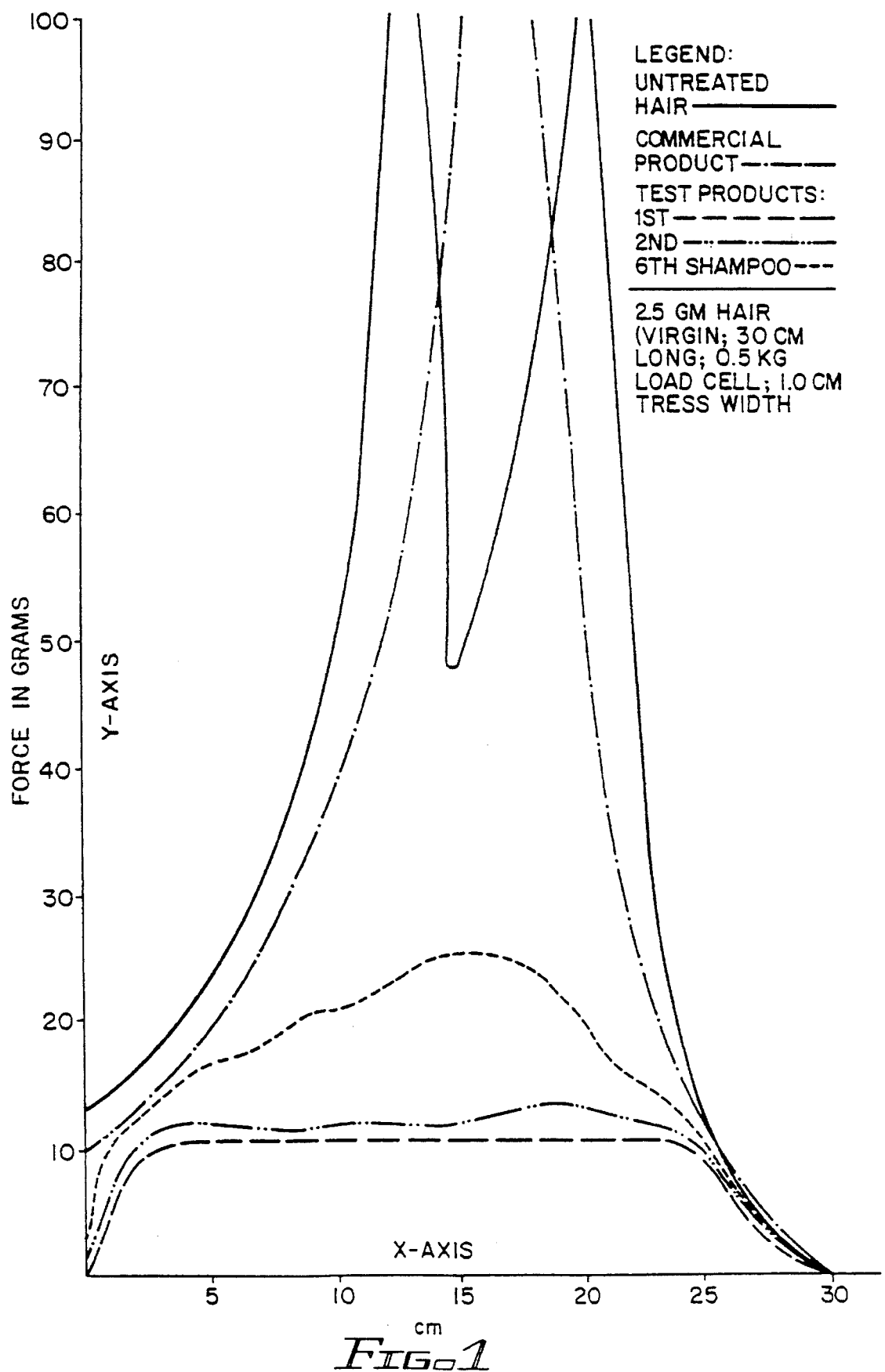
FIG. 1 demonstrates the effect of hair conditioning compositions on frictional force measurements done on hair tresses.

The hair treating compositions of this invention include a low viscosity oil-in-water emulsion of a mixture of a hydroxy terminated dimethyl polysiloxane having the general formula:

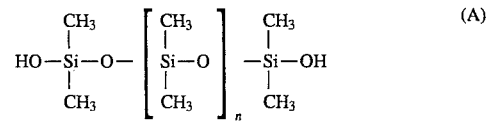
(A)

where n is not less than 500, and more specifically ranging from about 530 to about 675 and having a molecular weight of from about 40,000 to about 50,000 and a methyl hydrogen polysiloxane having the general formula:

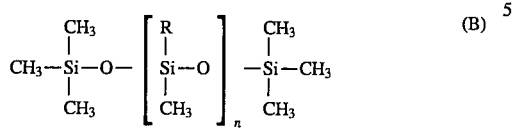

where n is from about 185–235 and having a molecular weight ranging from about 12,800 to about 17,000 and where R=H or $CH_3$ and further where the ratio of R=H to R=$CH_3$ is about 1:3.

The aforementioned polymers, although reactive, are maintained in the composition in an unreacted state and the crosslinking of the two polymers does not occur until the composition is applied to the hair and drying has taken place. The ratio of the polymers in the composition ranges from about 1 part of polymer A to about 1 part of polymer B (1:1) to about 100 parts of A to 1 part of B (100:1) with a preferred ratio of about 10 parts of A to 1 part of B (10:1). The total concentration of polymers in the composition is from about 0.5% to about 10% by weight. Very effective compositions are provided having a total concentration ranging from about 1% to about 5% by weight with a most preferred composition at about 4.4% and wherein the ratio of polymer A to polymer B is about 10:1. It is important that the composition have an acid pH, that is a pH ranging from about 2 to 6, preferably about 4. The pH may be adjusted in the usual manner with organic or inorganic acids which are customarily employed in toiletries, such as citric acid.

As previously noted, the compositions are in the form of an oil-in-water emulsion and thus the compositions include water and an appropriate emulsifier. Ethoxylated fatty alcohols having a chain length of $C_{12}$ to $C_{20}$ work well and are present in an amount ranging from about 0.10 to about 1% by weight. The composition may also include ingredients to enhance the substantively of the polymers to the hair, thickeners, colorants, perfumes, preservatives and the like. In incorporating perfume into the composition it is possible that perfume separation may result due to incomplete emulsification of the perfume oil. This can be remedied by ensuring that a sufficient level of emulsifier is included in the composition.

The hydroxy terminated dimethyl polysiloxane and methyl hydrogen polysiloxane are available as commercial products from Sandoz Chemicals Corporation under the trademarks "Sandoperm FE" and "Sandoperm FV" respectively. Sandoperm FE has a total solids level of 49% +/–3% with the level of hydroxymethyl polysiloxane at about 45%. Sandoperm FE also contains about 5% of $C_{12}$–$C_{20}$ branched chain ethoxylated fatty alcohol as well as from about 1% to about 2% of Amodimethicone (CTFA name) for added substantivity. Amodimethicone is a silicone polymer end blocked with amino functional groups and conforms generally to the formula:

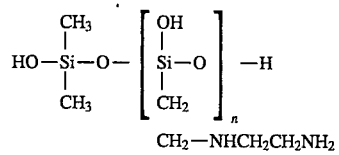

Sandoperm FV has a total solids level of about 40% +/–3%, about 35% of methyl hydrogen polysiloxane and about 5% of an ethoxylated polyethylene glycol nonyl phenyl alcohol as an emulsifier.

In order to demonstrate the effectiveness of the compositions and methods, the hair conditioning effects of the composition of Example I below, were quantified by frictional force measurements on hair tresses, using a model Instron universal testing instrument manufactured by the Instron Corporation. Hair tresses made with natural human hair (30cm long weighing 2.5+/–0.2gms) were treated by soaking them for one minute, in the composition of Example I, followed by squeezing out the excess material prior to drying. The hair treating composition was not rinsed out, although it may be rinsed out without adversely affecting the conditioning effect or its permanency. A similar set of tresses was treated with a leading commercial hair conditioner available under the trademark "Flex" (Regular Conditioner), with the product being rinsed out of the hair tresses prior to drying, as is customary with that type product.

The Instron instrument was fitted with a 0.5kg load cell for the test and the test was conducted at a crosshead speed of 200 mm/minute, using a comb 15 mm wide with average interteeth separations. All measurements were conducted on wet hair.

Referring to FIG. 1, average data is plotted, with the force in grams on the y-axis and the distance travelled by the comb down the hair shaft, on the x-axis. FIG. 2 shows the degree of damage to the hair which is plotted versus the number of washings. It was found that combing force measurements made under equal conditions, after the tresses were shampooed once with a commercial shampoo for normal hair, show force differences between the test product (i.e., Example I) and the untreated hair and hair treated with the commercial product of greater than ten fold in some regions of the hair shaft, particularly at the ends. The single dashed line shown in FIG. 1 reveals that for hair treated with a composition of this invention, the force required to comb the tresses barely exceeds 0.01kg for the greater portion of the length of the hair. The noise in the signal (or lack thereof), which is associated with the roughness of the hair surface, is virtually absent on the curve for hair treated with the composition of this invention. It shows no significant undulations. This indicates the polysiloxane composition left the hair smooth. In contrast, plots for the untreated control and the tresses treated with the commercial product after one shampoo are average envelope curves representing extremely jagged curves hard to reproduce in a diagram. These curves show that, after one shampooing, the hair treated with a leading commercial competitive product is just about as difficult to comb as combing hair that has not been treated. The conditioning treatment is washed out, while the treatment using a composition of this invention remains. The conditioning effect of the instant composition was measured after each of six consecutive shampooings, although FIG. 1 shows only the data for the first, second and sixth treatments.

In further tests, a statistically designed half head salon test was conducted with 20 subjects, mimicking the treatment protocol used in the force measurement study previously described and shown in FIG. 1. The commercial product and a product of this invention were applied randomly to the left and right sides of the subject's head and compared for three wet hair performance attributes before blow drying and for twelve dry hair performance attributes after blow drying. In addition, seven of the twelve dry hair attributes were re-evaluated twenty-four hours after the treatment. Furthermore, the subjects were given questionnaires focussing on six dry hair evaluations and one overall preference rating.

The results of this study are best understood by reviewing the data shown in Tables 1, 2 and 3. The ratings correspond to a three point scale as follows: 0=no difference, 1=small difference, 2=obvious difference and 3=great difference. Significant differences at the 80%, 90% and 95% confidence level are marked with appropriate superscripts. As used herein "test product" shall mean the product of Ex. I.

The data in Table 1 show that when the products were first applied the test product rated significantly (95%) better than the commercial control for three key dry hair conditioning attributes: "fewer snarls", "less comb drag" and "smoother feel". All other dry attributes were essentially at parity except for "manageability" for which the commercial control product was found better at the 80% confidence level. Of the wet hair conditioning attributes, the test product was rated better than the commercial control for "less comb drag" at the 80% confidence level, but just directionally better for "wet detangling".

After the first shampoo when neither one of the products was reapplied (i.e., day 2) the test product was found superior in several wet and dry conditioning attributes at the 95% confidence level. (See the second column marked Day 2 in Table 1). These data are in agreement with the Instron force measurements discussed earlier.

TABLE 1

OPERATOR'S RATINGS
STANDARD PRE- AND POST-TREATMENT
EVALUATION
(After Initial Application With No Reapplication of Products)
Rating Differences; Test Product Minus (−) Commercial Product

| Attribute | Day 1 | Day 2 | Day 3 | Day 4 | Day 5 |
|---|---|---|---|---|---|
| WET EVALUATIONS | | | | | |
| Detangling (Wet) | .35 | 1.30* | .85 | .85* | .55* |
| Less Comb Drag (Wet) | .55@ | 1.15* | .85* | .70* | .30* |
| Cleaner Feel (After Rinse) | −.10 | −.05 | −.05 | .05 | .05 |
| DRY EVALUATIONS | | | | | |
| Fewer Snarls (Dry) | .85* | 1.35* | .75* | .60* | .25# |
| Less Comb Drag (Dry) | .75* | 1.35* | .55* | .60* | .25# |
| Less Static | −.25 | .30@ | −.05 | .10 | .00 |
| Less Flaking | .00 | .00 | .00 | .00 | .00 |
| More Luster | .20@ | .15 | .05 | .20@ | .05 |
| More Bulk/Fullness | −.05 | .20@ | .10 | −.10 | .00 |
| More Bounce/Spring | −.05 | .50* | .40* | .35* | .05 |
| More Body | .00 | .30* | .25# | .25* | .00 |
| More Manageability | −.25@ | .45* | .05 | .05 | .00 |
| Cleaner Feel (Dry) | −.25 | −.10 | .00 | .05 | .00 |
| Less Tackiness | .00 | .00 | .00 | .00 | .00 |
| Smoother Feeling | .70* | .85* | .40* | .25# | .30# |

@, # and * - difference significant with 80%, 90% or 95% confidence, respectively. Values given are the differences in the beauticians ratings of the test product minus the commercial product.

TABLE 2

OPERATOR'S RATINGS
24 HOUR EVALUATION
Rating Differences; Test Product Minus (−) Commercial Product

| Attribute | Day 2 | Day 3 | Day 4 | Day 5 |
|---|---|---|---|---|
| Fewer Snarls | .80* | .35# | .50* | .50* |
| Less Comb Drag | .85* | .45* | .30* | .30* |
| More Bulk/Fullness | .20 | .05 | .00 | −.10 |
| More Bounce/Spring | .30# | .20 | .10 | .00 |
| Less Greasy/Cleaner Feel | −.15 | −.10 | .05 | .00 |
| More Curl Retention | .25# | .25@ | .20@ | .00 |
| Better Appearance | .15 | .10 | .20@ | −.05 |

@, # and * - difference significant with 80%, 90% or 95% confidence, respectively.

TABLE 3

SUBJECT'S SELF-EVALUATIONS
AMONG SUBJECTS WITH A PREFERENCE (I.E.
IGNORING "NO PREF" RESPONSES), THE
TABLE ENTRIES ARE THE PERCENT OF SUBJECTS
CHOOSING THE TEST PRODUCT OVER THE COMMERCIAL PRODUCT FOR THE LISTED ATTRIBUTES
% Choosing Test Product over Commercial Product
(No Diff = 50%)

| Attribute | Initial | Day 2 | Day 3 | Day 4 | Day 5 |
|---|---|---|---|---|---|
| After Running Comb/Brush Through Hair: | | | | | |
| Stay in Place Better | 55 | 50 | 63 | 71@ | 56 |
| Looks Fuller/Thicker | 55 | 65@ | 61 | 89* | 56 |
| After Running Fingers Through Hair: | | | | | |
| Stay in Place Better | 50 | 50 | 53 | 71# | 59 |
| Looks Fuller/Thicker | 55 | 56 | 40 | 82* | 53 |
| Hair Feels Better | 44 | 35@ | 62 | 62 | 45 |
| Healthier-Looking | 56 | 53 | 64 | 62 | 64 |
| Prefer Overall | 55 | 61 | 55 | 72# | 65@ |

@, # and * - difference from 50% significant with 80%, 90 or 95% confidence, respectively. The percentage of subjects choosing Test Product over Commercial Product in the Table is calculated ignoring ties, which number from 0 to 9 of the 20 subjects.

As further shown in Table 1, for days 3 and 4 these differences persist (after 2 and 3 shampooings) but the significance of the difference wanes by the fourth shampoo (Day 5), except for wet detangling and wet comb drag which are still superior at the 95% confidence level and for the dry attributes of fewer snarls and less comb drag. Again these data are in agreement with the Instron data shown in FIG. 1.

The evaluation after 24 hours shown in Table 2 clearly demonstrates one of the attributes of the present invention, that is, superior, long-lasting curl retention properties. This attribute is originally seen, in Table 1, as a composite of two attributes "more bounce/spring" and "more body". The ratings shown in Table 2 for more curl retention correlate with the ratings for fewer snarls (as hair curls fallout while sleeping and the hair gets snarled); particularly taking into consideration that the panelists were not allowed to touch-up their hairdos.

Another attribute of the present invention is the delivery of conditioning benefits over a longer period of time without making the hair feel coated, greasy or stiff. In Tables 1 and 2, the ratings for cleanliness are consistently at parity with the side which was not treated with the test product any further after the first shampoo, i.e., the residue on the hair is equal to freshly shampooed hair.

The subjects were requested to do a preference evaluation by running the comb or brush through their hair once (without setting it or rearranging the set) for a visual and a tactile evaluation, for five conditioning attributes. As shown in Table 3, the subjects overall preference was for the test product over the five days of the test. It is noteworthy that the number of patrons preferring the test product grew to a maximum at day 4. The difference over a split (50/50), was significant at the 90% confidence level, at this point 72% versus 28 %.

This trend is borne out in every attribute tested, e.g., the preference for "looks fuller/thicker" increased from a 55%/45% split to 89%/11% at day 4. This difference is significant at the 95% confidence level. A similar result was obtained whether the evaluation was done by combing through the hair or by running the fingers through it.

The number of subjects preferring the test product for "(hair) stays in place better, i.e. holding the set" also increased from a 50/50 split to 71% preferring the test product, a significant difference.

The fact that the number of subjects preferring the side of their head treated with the test product increased with the number of shampooings, perhaps can be explained as a hair protecting mechanism against the harshness of shampooing every day, i.e. as the untreated hair gets stripped further and further by the washing action, the differences between the treated versus the untreated hair increases, until the fourth day on the third shampooing after treatment. In reality, both sides of the head are being "damaged" by shampooing, but at different rates.

This is best understood by again examining the diagram of FIG. 2 wherein the degree of damage to the hair is plotted against the number of washings. At day 1 the hair treated with the test product is perceived to be equal in condition or slightly better than the side treated with the commercial product, i.e., $Y_1$ is small. After washings one and two the difference between the treatments increases, ($Y_2$ & $Y_3$) but the differences are not numerically significant. After the third washing ($Y_4$) the difference is maximum and also numerically significant; thereafter the difference begins to narrow ($Y_5$), ($Y_6$) etc.

The following specific Examples disclose useful hair treating compositions according to the present invention.

EXAMPLE I

| Example I | |
|---|---|
| Ingredient | % by Weight |
| Hydroxy Dimethyl Polysiloxane | 2.000 |
| Methyl Hydrogen Polysiloxane | 0.156 |
| Emulsifying Surfactant; Ethoxylated fatty alcohol (cetyl/lauryl) | 2.244 |
| Water, DI | 95.600 |
| | 100.000 | pH adjusted with citric acid (30%) to 4

EXAMPLE II

| Example II (Product with improved static control) | |
|---|---|
| Ingredient | % by Weight |
| Sandoperm FE | 4.00 |
| Sandoperm FV | 0.40 |
| Antistatic Agent (Stearyldimethylbenzyl ammonium chloride) | 0.50 |
| Fragrance | 0.10 |
| Water, DI | 95.00 |
| | 100.0 | pH adjusted to 4 with 30% citric acid

EXAMPLE III

| Example III | | |
|---|---|---|
| | % by Weight | |
| Ingredient | A | B |
| Sandoperm FE | .50 | 1.00 |
| Sandoperm FV | 0.50 | 0.10 |
| *Polyurethane QW 4019 | 2.00 | 4.00 |
| SD 40 190 | 77.00 | 64.90 |
| Water, DI | 20.00 | 30.00 |
| | 100.00 | 100.00 |

*obtained from Grace Chemicals

EXAMPLE IV

| Example IV | |
|---|---|
| Ingredient | % by Weight |
| Sandoperm FE | 4.00 |
| Sandoperm FV | 0.40 |
| Water, Deionized | 95.60 |

Adjust pH to 4.0 with 30% citric acid/cold blend by adding polysiloxanes to water. This composition is useful as a conditioner, as such, or in a pump spray package.

Adjust pH to −4.0 with 30% citric acid/clod blend by adding polsiloxanes to water.

This composition is useful as a conitioner, as such, or in a pump spray package.

EXAMPLE V

| Example V | |
|---|---|
| Ingredient | % by Weight |
| Sandoperm FE | 4.00 |
| Sandoperm FV | 0.40 |
| Fragrance | 0.30 |
| Dye D&C Green #5 (0.1% in DI. Water) | 0.30 |
| Carbopol 1342* | 0.50 |
| Water, DI | 94.50 |

*Carbopol 1342 is a copolymer of acrylic acid and a long chain alkyl methacrylate and available from B.F. Goodrich Company. It functions as a thickener and can serve as an emulsifier for oil-in-water emulsions.

Adjust pH to 4.0 with 10% TEA. Viscosity :193.1K cps LVT sp.TC, @12 rpm.

This composition is useful as a semi-permanent hair conitioner rise.

EXAMPLE VI

| Example VI | |
|---|---|
| Ingredient | % by Weight |
| Sandoperm FE | 4.00 |
| Sandoperm FV | 0.40 |
| Fragrance | 0.30 |
| Dye D&C Green #5 (0.1% in DI. Water) | 0.30 |
| Xanthan Gum Keltrol Food Grade | 0.50 |
| Water, DI | 94.50 |

Adjust pH to 4.0 with 30% Citric Acid. Viscosity 820 cps. Brookfield Viscometer Model LVT, Spindle #2 at 30 rpm.

This composition is useful as a semi-permanent hair conditioner or creme rinse.

Further tests were conducted as follows:

Analysis Combined Over Hairtype

A study was made to compare the test product to a commercial hair conditioner in a 5-day, "half-head" study in which the test product was applied only on the first day while the commercial product was applied on each of the 5 days of the study. The purpose was to determine the number of days until the conditioning benefits imparted by a single application of the test product would decline to the level of daily applications of the commercial conditioner. The results of this study are shown in Tables 4–6. The ratings correspond to the following scale:

0=no difference

1=small difference

2=obvious difference

3=great difference

It should be noted that the salon operators were blinded to the treatments when evaluating but the subjects were not blinded to the treatments on days 2 through 5 since they experienced treatment application on only one side of the head during those days. Thus, a placebo effect may partly account for the fact that the subject's self evaluations tended to favor the commercial product on days 2, 3 and especially 4. Their evaluations seem to indicate that "reality" took over by day 5 and the test product was again indicated as superior.

TABLE 4

OPERATOR'S RATINGS
STANDARD PRE- AND POST-TREATMENT
EVALUATION
Treatment Differences; (Test Product Minus (−) Commercial Product

| Attribute | Initial | Day 2 | Day 3 | Day 4 | Day 5 |
|---|---|---|---|---|---|
| WET EVALUATIONS | | | | | |
| Detangling (Wet) | .62* | .55* | 1.10* | 1.02* | .76* |
| Less Comb Drag (Wet) | .54* | .78* | 1.10* | 1.19* | .76* |
| Cleaner Feel (After Rinse) | .00 | .12@ | .04 | .00 | .00 |
| DRY EVALUATIONS | | | | | |
| Fewer Snarls (Dry) | .86* | .74* | .83* | .64* | .64* |
| Less Comb Drag (Dry) | .83* | .88* | .83* | .74* | .70* |
| Less Static | .07 | .11 | .05 | .00 | .08 |
| Better Overall Appearance | .30* | .44* | .43* | .33# | .49* |
| More Luster | .00 | .15 | .20* | .04 | .23* |
| More Bulk/Fullness | .03 | .46* | .11 | .10 | .42* |
| More Bounce/Spring | .15 | .53* | .41* | .14 | .38* |
| More Body | .15 | .59* | .33* | .24@ | .38* |
| More Manageability | .10 | .49* | .23* | .12 | .24@ |
| Cleaner Feel (Dry) | −.01 | .01 | .00 | .00 | .00 |
| More Curl Retention | −.09 | .37* | .12# | −.04 | .16 |
| Smoother Feel | .17# | .25# | .35* | .29* | .21@ |

@, # and * - difference significant with 80%, 90% or 95% confidence, respectively.

TABLE 5

OPERATOR'S RATINGS
"MORNING AFTER" EVALUATION
Treatment Differences; (Test Product Minus (−) Commercial Product

| Attribute | Day 2 | Day 3 | Day 4 | Day 5 |
|---|---|---|---|---|
| Fewer Snarls | .53* | .55* | .66* | 1.10* |
| Less Comb Drag | .67* | .55* | .73* | 1.10* |
| Less Static | .00 | .00 | −.05 | .00 |
| More Bulk Fullness | −.01 | .22@ | .29* | .19 |
| More Bounce/Springiness | .48* | .40* | .23* | .25@ |
| More Manageability | .37* | .31* | .08@ | .02 |
| Less Greasy (Cleaner Feel) | −.05 | −.13@ | .00 | −.01 |
| More Curl Retention | .35* | .15# | .04 | −.03 |
| Better Appearance | .25 | .56* | .34* | .36# |

@, # and * - difference significant with 80%, 90% or 95% confidence, respectively.

TABLE 6

SUBJECT'S SELF-EVALUATIONS
Among Subjects With a Preference (I.E. Ignoring "No Pref"
Responses) the Table Entries are the Percent of Subjects
Choosing the Test Product Over Commercial Conditioner for
the Listed Attribute.
% Choosing Test Product over Commercial Product
(No Diff = 50%)

| Attribute | Initial | Day 2 | Day 3 | Day 4 | Day 5 |
|---|---|---|---|---|---|
| After Running Comb/Brush Through Hair: | | | | | |
| Stays in Place Better | 52 | 56 | 48 | 36@ | 52 |
| Looks Fuller/Thicker | 40 | 48 | 48 | 35@ | 50 |
| After Running Fingers Through Hair: | | | | | |
| Stays in Place Better | 52 | 67@ | 40 | 35@ | 52 |
| Looks Fuller/Thicker | 42 | 54 | 46 | 35@ | 48 |
| Hair Feels Better | 50 | 54 | 46 | 43 | 64@ |
| Healthier-Looking | 36@ | 57 | 32# | 32# | 50 |
| Prefer Overall | 48 | 64@ | 40 | 40 | 54 |

@, # and * - difference from 50% significant with 80%, 90% or 95% confidence, respectively. The percentage choosing test product over commercial conditioner is calculated ignoring ties, which number from 0 to 9 of the 20 subjects.

Analysis bY Hair type

Tables 7 and 8 summarize a statistical analysis comparing the 2 hair types, "dry" vs. "normal", in terms of the relative performance of the test product and the commercial conditioner. Hair classified as dry is generally colored and/or permed hair and is considered to have some damage. Only the Hair Salon Operator Ratings were analyzed in this way; self-evaluations were not analyzed by hair type since to do so would have produced an overly scarce contingency table (see below).

TABLE 7

OPERATOR'S RATINGS
STANDARD PRE- AND POST-TREATMENT
EVALUATION BY HAIR TYPE
Treatment Differences; (Test Product Minus (−) Commercial Product)

| Attribute | HairType | Initial | Day 2 | Day 3 | Day 4 | Day 5 |
|---|---|---|---|---|---|---|
| WET EVALUATIONS | | | | | | |
| Detangling (Wet) | Dry | .79 | .64 | 1.29 | 1.14 | .71 |
| | Normal | .46 | .45 | .91 | .90 | .80 |

TABLE 7-continued

OPERATOR'S RATINGS
STANDARD PRE- AND POST-TREATMENT
EVALUATION BY HAIR TYPE
Treatment Differences; (Test Product Minus (-) Commercial Product)

| Attribute | HairType | Initial | Day 2 | Day 3 | Day 4 | Day 5 |
|---|---|---|---|---|---|---|
| Less Comb | Dry | .86@ | .94 | 1.29 | 1.07 | .71 |
| Drag | Normal | .22 | .65 | .91 | 1.30 | .80 |
| Cleaner | Dry | .00 | .14 | .07 | .00 | .00 |
| Feel | Normal | .00 | .09 | .00 | .00 | .00 |
| DRY EVALUATIONS | | | | | | |
| Fewer | Dry | 1.21* | .93 | .93 | .57 | .29# |
| Snarls (Dry) | Normal | .50 | .56 | .73 | .70 | .99 |
| Less Comb | Dry | 1.14# | .93 | .93 | .79 | .43 |
| Drag (Dry) | Normal | .52 | .83 | .73 | .70 | .96 |
| Less Static | Dry | .14 | .21 | .00 | .00 | .00 |
| | Normal | .00 | .00 | .09 | .00 | .17 |
| Better Overall Appear. | Dry | .64* | .71# | .57 | .36 | .64 |
| | Normal | -.05 | .18 | .27 | .30 | .34 |
| More Luster | Dry | .07 | .29 | .21 | .07 | .29 |
| | Normal | -.07 | .02 | .18 | .00 | .18 |
| More Bulk/ Fullness | Dry | .36* | .50 | .21 | .00 | .43 |
| | Normal | -.30 | .43 | .01 | .20 | .41 |
| More Bounce/ Spring | Dry | .50* | .79# | .64@ | .07 | .43 |
| | Normal | -.20 | .27 | .18 | .20 | .33 |
| More Body | Dry | .50* | .92* | .57# | .29 | .43 |
| | Normal | -.20 | .25 | .09 | .20 | .33 |
| More Manage- ability | Dry | .42* | 71@ | .28 | .14 | .14 |
| | Normal | -.22 | .26 | .18 | .10 | .33 |
| Cleaner Feel | Dry | .14 | -.07 | .00 | .00 | .00 |
| | Normal | -.17 | .08 | .00 | .00 | .00 |
| More Curl Retention | Dry | .14 | .57# | .14 | -.07 | .07 |
| | Normal | -.31 | .16 | .09 | .00 | .26 |
| Smoother Feel | Dry | .13 | .22 | .42 | .28 | .14 |
| | Normal | .19 | .28 | .27 | .30 | .27 |

@, # and * - Dry vs. Normal Hair types significantly different with 80%, 90% or 95% confidence, respectively.

TABLE 8

OPERATOR'S RATINGS
"MORNING AFTER" EVALUATION
Treatment Differences; (Test Product Minus (-) Commercial Conditioner)

| Attribute | Hair Type | Day 2 | Day 3 | Day 4 | Day 5 |
|---|---|---|---|---|---|
| Fewer Snarls | Dry | .50 | .86 | .42# | 1.42* |
| | Normal | .55 | .25 | .88 | .75 |
| Less Comb Drag | Dry | .64 | .86* | .50* | 1.42* |
| | Normal | .70 | .25 | .97 | .75 |
| Less Static | Dry | .00 | .00 | .00 | .00 |
| | Normal | .00 | .00 | -.09 | .00 |
| More Bulk/ Fullness | Dry | .30 | .36 | .21 | .36 |
| | Normal | -.31 | .08 | .37 | .02# |
| More Bounce/ Spring | Dry | .71@ | .64# | .28 | .50# |
| | Normal | .25 | .17 | .18 | .01 |
| More Manage- ability | Dry | .71* | .50@ | .07 | .14 |
| | Normal | .03 | .11 | .09 | -.10 |
| Less Greasy | Dry | -.07 | .07* | .00 | .00 |
| | Normal | -.03 | -.33 | .00 | -.01 |
| More Curl Retention | Dry | .57# | .21 | .07 | .14# |
| | Normal | .13 | .08 | .00 | -.17 |
| Better Appearance | Dry | .50 | 1.00* | .14@ | .64@ |
| | Normal | .01 | .12 | .55 | .08 |

@, # and * - Dry vs. Normal Hair types significantly different with 80%, 90% and 95% confidence, respectively.

Statistical Methods

The data included the "Standard Pre- and Post-Treatment Evaluations" by the salon operators, "Morning After" Evaluations by the salon operators and "Self-Evaluations" by the subjects. All operators' ratings were analyzed using an analysis of variance which accounted for variation due to differences among hair types, differences among subjects within hair types, differences in side of head, differences between the treatments and the interaction of treatments with hair types. Subjects' Self-Evaluations were paired choice responses where the subject chose which side had more of each attribute. These data were analyzed using a 2-by-2 table which tabulated subjects by Preferred-Side-of-Head (left vs. right) and Treatment/Side-Assignment (A→Left/B→Right vs. B→Left/A→Right). Subjects' Self-evaluations were not analyzed by hair type since to do so would have produced an overly sparce contingency table: cross classification of 20 subjects by 8 categories (Preferred-Side-of-Head) (Left vs Right), Treatment/Side-Assignment (A→Left/B→Right vs B→Left/A→Right) and Hair type (Dry vs Normal).

The following examples disclose additional useful compositions for treating hair.

EXAMPLE VII

| Example VII | |
|---|---|
| Ingredient | % by Weight |
| Sandoperm FE | 4.000000 |
| Sandoperm FV | 0.400000 |
| Fragrance 05-10 | 0.300000 |
| Dye Green #5 0.1% in H2O | 0.300000 |
| Hydantoin 55 | 0.500000 |
| Methyl Paraben | 0.150000 |
| Propyl Paraben | 0.050000 |
| Xanthan Gum 1.0% in Water | 50.000000 |
| Water, DI | 44.300000 |

Adjust pH to 4.0 with 30% Citric Acid Hydantoin, Methyl Paraben and Propyl Paraben used as a preservative

EXAMPLE VIII

| Example VIII | |
|---|---|
| Ingredient | % by Weight |
| Sandoperm FE | 4.000000 |
| Sandoperm FV | 0.400000 |
| Fragrance 05-10 | 0.300000 |
| Dye Green #5 0.1% in Water | 0.300000 |
| Hydantoin 55 | 0.500000 |
| Water, Deionized | 94.500000 |

Adjust pH to 4.0 with 30% Citric Acid aqueous.
Low viscocity product.

EXAMPLE IX

| Example IX | |
|---|---|
| Ingredient | % by Weight |
| Sandoperm FE Liquid | 4.000000 |
| Sandoperm FV Liquid | 0.400000 |
| Fragrance 06-37 | 0.150000 |

EXAMPLE IX

| Ingredient | % by Weight |
| --- | --- |
| FD&C Green #5 | 0.000300 |
| DMDM Hydantoin (55%) | 0.500000 |
| Water, Deionized | 94.949700 |

Adjust pH to 4.0+/−0.5 with 30% citric acid

EXAMPLE X

| Ingredient | % by Weight |
| --- | --- |
| Sandoperm FE Liquid | 4.000000 |
| Sandoperm FV Liquid | 0.400000 |
| Fragrance 06-37 | 0.075000 |
| FD&C Green #5 | 0.000300 |
| DMDM Hydantoin (55%) | 0.500000 |
| Water, Deionized | 95.024700 |

Adjust pH to 4.0+/−0.5 with Citric Acid (30% Aq.)

EXAMPLE XI

| Ingredient | % by Weight |
| --- | --- |
| Sandoperm FE Liquid | 2.000000 |
| Sandoperm FV Liquid | 0.200000 |
| Fragrance 06-37 | 0.075000 |
| FD&C Green #5 | 0.000300 |
| DMDM Hydantoin (55%) | 0.500000 |
| Water, Deionized | 97.224700 |

Adjust pH to 4.0+/−0.5 with Citric Acid (30% Aq.)

EXAMPLE XII

| Ingredient | % by Weight |
| --- | --- |
| Sandoperm FE Liquid | 1.000000 |
| Sandoperm FV Liquid | 0.100000 |
| Fragrance 06-37 | 0.075000 |
| FD&C Green #5 | 0.000300 |
| DMDM Hydantoin (55%) | 0.500000 |
| Water, Deionized | 98.324700 |

Adjust pH to 4.0+/−0.5 with Citric Acid (30% Aq.)

EXAMPLE XIII

| Ingredient | % by Weight |
| --- | --- |
| Sandoperm FE Liquid | 1.000000 |
| Sandoperm FV Liquid | 0.100000 |
| Fragrance 06-37 | 0.075000 |
| DMDM Hydantoin (55%) | 0.500000 |
| Water, Deionized | 98.325000 |

Adjust pH to 4.0+/−0.5 with Citric Acid (30% Aq.)

EXAMPLE XIV

| Ingredient | % by Weight |
| --- | --- |
| Sandoperm FE Liquid | 2.000000 |
| Sandoperm FV Liquid | 0.200000 |
| Fragrance 06-37 | 0.075000 |
| DMDM Hydantoin (55%) | 0.500000 |
| Water, Deionized | 97.225000 |

Adjust pH to 4.0+/−0.5 with Citric Acid (30% Aq.).

EXAMPLE XV

| Ingredient | % by Weight |
| --- | --- |
| Sandoperm Fe Liquid | 4.000000 |
| Sandoperm FV Liquid | 0.400000 |
| Fragrance 06-37 | 0.075000 |
| DMDM Hydantoin (55%) | 0.500000 |
| Water, Deionized | 95.025000 |

Adjust pH to 4.0+/−0.5 with Citric Acid (30% Aq.)

EXAMPLE XVI

| Ingredient | % by Weight |
| --- | --- |
| Sandoperm FE Liquid | 4.000000 |
| Sandoperm FV Liquid | 0.400000 |
| Fragrance 06-37 | 0.075000 |
| DMDM Hydantoin | 0.500000 |
| Water, Deionized | 94.950000 |

The level of active Kathon CG is 11.25 PPM adjust pH to 4.0+/−with Citric Acid (30% Aq.).

EXAMPLE XVII

| Ingredient | % by Weight |
| --- | --- |
| Sandoperm FE Liquid | 1.000000 |
| Sandoperm FV Liquid | 0.100000 |
| Fragrance 06-37 | 0.075000 |
| Dantoin DMDMH-55 | 0.500000 |
| Kathon CG (as sold) | 0.075000 |
| Water, Deionized | 98.250000 |

The level of active Kathon CG is 11.25 PPM. Adjust pH to just under 4.0 with Citric Acid (30% Aq.).

EXAMPLE XVIII

| Ingredient | % by Weight |
| --- | --- |
| Sandoperm FE Liquid | 4.000000 |
| Sandoperm FV Liquid | 0.400000 |
| Fragrance 06-37 | 0.075000 |
| Dantoin DMDMH-55 | 0.500000 |
| Kathon CG (as sold)* | 0.050000 |

-continued

Example XVIII

| Ingredient | % by Weight |
| --- | --- |
| Methylparaben USP/NF | 0.200000 |
| EDTA.NA2 | 0.100000 |
| Water, Deionized | 94.675000 |

The level of active Kathon CG is 7.5 PPM. Adjust pH to just under 4.0 with Citric Acid (30% Aq.).

*Kathon CG is a preservative available from Rohm & Haas. The active ingredient is methylchloroisothiazolinone which conforms to the formula:

$$\underset{\text{Cl}}{\underset{\|}{\phantom{x}}}\overset{S}{\diagdown}\underset{\phantom{x}}{\overset{\diagup}{\text{N—CH}_3}}=O$$

EXAMPLE XIX

| Ingredient | % by Weight |
| --- | --- |
| Sandoperm FE Liquid | 1.000000 |
| Sandoperm FV Liquid | 0.100000 |
| Fragrance 06-37 | 0.075000 |
| Dantoin DMDMH-55 | 0.500000 |
| Kathon CG (as sold) | 0.050000 |
| Methylparaben USP/NF | 0.100000 |
| Water, Deionized | 97.975000 |

The level of active Kathon CG is 7.5 PPM. Adjust pH to just under 4.0 with Citric Acid (30% Aq.).

To use the conditioning compositions, the hair may be shampooed and towel dried. Thereafter the composition is applied to the hair followed by working in the hair with the fingers. The treated hair may then be combed and dried in the customary manner. Blow drying with heated air gives longer lasting conditioning. For users who want to style their hair, any one of the following procedures will give acceptable results.

1) After shampooing the hair is air dried. Thereafter the conditioner is applied and then the hair is curled while still damp.

2) Application of the conditioning composition after shampooing, then placing the hair on rollers while still wet followed by blow drying.

3) Application of the conditioning composition to the hair followed by drying. Thereafter the hair is rewetted slightly, placed on rollers or a curling iron may be used and thereafter the hair is dried.

4) The hair is treated with the conditioning composition, then blow dried until slightly moist to the touch and then placed on rollers or curled in the customary way.

In the foregoing, a styling mousse or gel may also be applied to the hair after applying the conditioning composition.

I claim:

1. A composition for semi-permanently conditioning hair comprising an aqueous oil-in-water emulsion of a mixture of (1) a hydroxy-terminated dimethyl polysiloxane having the general formula $$HO-\underset{CH_3}{\overset{CH_3}{Si}}-O-\left[\underset{CH_3}{\overset{CH_3}{Si}}-O\right]_n-\underset{CH_3}{\overset{CH_3}{Si}}-OH$$

where n is not less than 500 and (2) a methyl hydrogen polysiloxane having the general formula $$CH_3-\underset{CH_3}{\overset{CH_3}{Si}}-O-\left[\underset{CH_3}{\overset{CH_3}{Si}}-O\right]_n-\underset{CH_3}{\overset{CH_3}{Si}}-CH_3$$

where n is from about 185–235 and where R is selected from the group consisting of H or $CH_3$ and where the ratio of R=H to R=$CH_3$ is about 1:3, said composition being at an acid pH and wherein the ratio of polysiloxane (1) to polysiloxane (2) is about 1:1 to about 100:1 with the total concentration of said polysiloxanes being from about 0.5% to about 10% by weight of said composition, said polysiloxanes in said composition prior to application to said hair being in an unreacted state.

2. The composition of claim 1 wherein the value of n in polysiloxane (1) is from about 530 to about 675 and wherein the ratio of polysiloxane (1) to polysiloxane (2) is about 10:1 and wherein said composition additionally includes about 0.10 to about 1% by weight of an emulsifier.

3. The composition of claim 2 wherein the concentration of said polysiloxanes is from about 1% to about 5% by weight and wherein said emulsifier is an ethoxylated fatty alcohol having from 12 to 20 carbon atoms in the fatty portion of said alcohol.

4. The composition of claim 3 wherein said pH of said composition is from about 2 to about 6.

5. The composition of claim 4 wherein said pH is about 4.

6. The composition of claim 5 wherein said composition additionally includes an amodimethicone having the formula:

$$HO-\left[\underset{CH_3}{\overset{CH_3}{Si}}-O\right]-\left[\underset{\underset{CH_2-NHCH_2CH_2NH_2}{\overset{CH_2}{|}}}{\overset{OH}{\underset{|}{\overset{|}{Si}}-O}}\right]-H$$

* * * * *